(12) United States Patent
Adell

(10) Patent No.: US 9,717,568 B1
(45) Date of Patent: Aug. 1, 2017

(54) DENTAL DEVICE FABRICATION ON A 3-D PRINTED ARCH MODEL

(71) Applicant: Loren S. Adell, Sunnyvale, TX (US)

(72) Inventor: Loren S. Adell, Sunnyvale, TX (US)

(73) Assignees: Loren S. Adell, Sunnyvale, TX (US); Michael Adell, Sunnyvale, TX (US)

( * ) Notice: Subject to any disclaimer, the term of this patent is extended or adjusted under 35 U.S.C. 154(b) by 532 days.

(21) Appl. No.: 14/277,457

(22) Filed: May 14, 2014

(51) Int. Cl.
*A61C 5/10* (2006.01)
*A61C 7/00* (2006.01)
*A61C 13/00* (2006.01)

(52) U.S. Cl.
CPC .......... *A61C 7/002* (2013.01); *A61C 13/0004* (2013.01)

(58) Field of Classification Search
CPC ..................................... A61K 6/02; A61K 6/10
USPC .............................. 433/215, 217.1, 223, 226
See application file for complete search history.

(56) References Cited

U.S. PATENT DOCUMENTS

| 4,368,040 A * | 1/1983 | Weissman ............ A61C 9/0006 433/223 |
| 2004/0166462 A1* | 8/2004 | Phan ...................... A61C 7/146 433/24 |

* cited by examiner

*Primary Examiner* — Ellen C Hammond
*Assistant Examiner* — Christina Negrellirodrigue
(74) *Attorney, Agent, or Firm* — George L. Boller

(57) ABSTRACT

A dental arch model fabricated by a 3-D printing process is covered by conforming a liquid-dissolvable sheet of material onto a portion of the dental arch model to physically isolate material from which the dental arch model has been fabricated from material which will be used to fabricate an intra-oral device. The sheet material is a barrier which renders the material of the dental arch model and the material of the intra-oral device immune to chemical reaction with each other. After the device has been removed from the model, liquid is applied to the liquid-dissolvable material on the model. Instead of using a sheet as a barrier, a conditioning coating may be applied to the arch model, and a release coating is applied over the conditioning coating.

14 Claims, 3 Drawing Sheets

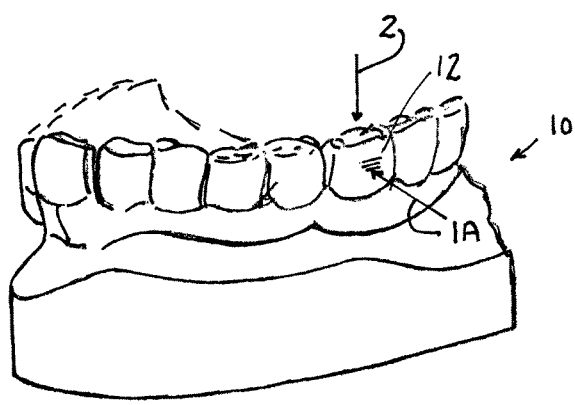
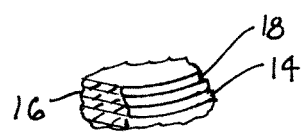
Fig. 1
Fig. 1A
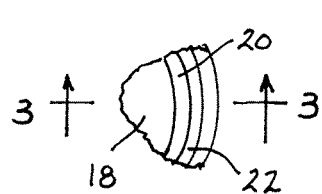
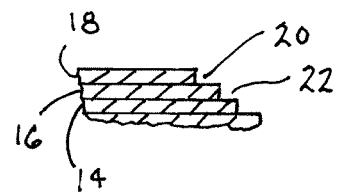
Fig. 2
Fig. 3

DENTAL DEVICE FABRICATION ON A 3-D PRINTED ARCH MODEL

TECHNICAL FIELD

This invention relates to dentistry. In particular the invention relates to fabrication of intra-oral devices on dental arch models which have been fabricated by 3-D printing.

BACKGROUND

Intra-oral devices which are applied to persons' dental arches, both orthodontic and non-orthodontic devices, have historically been made by casting a dental arch model from an impression of a person's dental arch and then fabricating the device on the cast arch model. Such a process is largely labor-intensive.

An arch impression, either total or partial, is typically taken at a dental office. While the device fabrication process can be completed at the dental office, an alternative is to send an arch impression to a dental laboratory where the process is completed, after which the finished device is sent to the dental office.

A significant factor in a dentist's decision to use a dental laboratory in that way is fabrication cost because use of technicians in a dental laboratory to fabricate an intra-oral device is likely to be more economical.

A more recent process for fabricating an intra-oral device utilizes 3-D printing to fabricate a dental arch model. An electronic scan of a person's arch is performed to create a data file which can be transmitted to a dental laboratory which has 3-D printing equipment for fabricating a dental arch model from the data file.

There are a number of commercial sources for 3-D scanners for scanning a person's arch, for software for converting a scan into a program for a 3-D printer, and for 3-D printers.

The 3-D printing process creates a 3-D model by a layering process in which each successive layer is laid down on top of a preceding one, thereby building the model one layer at a time. While each layer has a finite thickness which can be very small, the nature of the process may result in the layering having surface grooves because of non-congruence of perimeters of successive layers. While making the layers thinner reduces the size of the surface grooves, the length of time needed to fabricate a model may increase because of the need to increase the number of layers. Because the length of time for which a 3-D printer is in use affects the economics of creating a model, reducing the size of the surface grooves in that way may increase fabrication cost.

If the surface grooves in a printed arch model are significant enough to be considered imperfections, it may be necessary for a technician to manually work on the model using suitable tools to eliminate, or at least minimize, the imperfections. The amount of labor to do so is also a contributor to fabrication cost.

The costs associated with use of a 3-D printer for creating a model and any subsequent technician work on the model may therefore be seen to be a function of the degree of accuracy which is needed in a finished appliance. For certain appliances a high degree of accuracy may be needed to achieve acceptable functionality of the appliance and comfort of a person using a particular appliance.

SUMMARY OF THE INVENTION

Applicant has observed that because only certain raw materials are useful in the fabrication of a dental arch model by a 3-D printing process, a material which is desired to be used to fabricate an intra-oral device on a dental arch model which has been fabricated by a 3-D printing process may have certain incompatibilities with the material of the dental arch model which may contribute to fabrication cost in one way or another.

This disclosure provides methods for enabling potentially incompatible materials to be used and for reducing fabrication time. The disclosed methods are also useful with compatible materials because of fabrication time reduction.

General aspects of the disclosure relate to a method of fabricating intra-oral devices on dental arch models which have been fabricated by a 3-D printing process.

Generally speaking, the method comprises: fabricating a dental arch model of at least a portion of a person's dental arch by a 3-D printing process which creates multiple consecutive layers of a first material each laid down on top of a preceding layer; forming a barrier on at least a portion of the dental arch model which renders the first material of the dental arch model and a second material to be used to fabricate an intra-oral device, immune to chemical reaction with each other; fabricating the intra-oral device by forming the second material onto the portion of the dental arch model onto which the barrier has been formed; and removing the intra-oral device from the dental arch model.

The barrier may be a sheet which is conformed to at least a portion of a dental arch model. It may also be a conditioning coating which is created by wetting the model with a suitable solution and then drying the solution.

The foregoing summary, accompanied by further detail of the disclosure, will be presented in the Detailed Description below with reference to the following drawings that are part of this disclosure.

BRIEF DESCRIPTION OF THE DRAWINGS

FIG. 1 is a perspective view of a dental arch model which has been fabricated by a 3-D printing process.

FIG. 1A is a magnified fragmentary view in the direction of arrow 1A in FIG. 1.

FIG. 2 is a magnified fragmentary view in the direction of arrow 2 in FIG. 1.

FIG. 3 is a cross section view in the direction of arrows 3-3 in FIG. 2.

DETAILED DESCRIPTION

Figure 4:
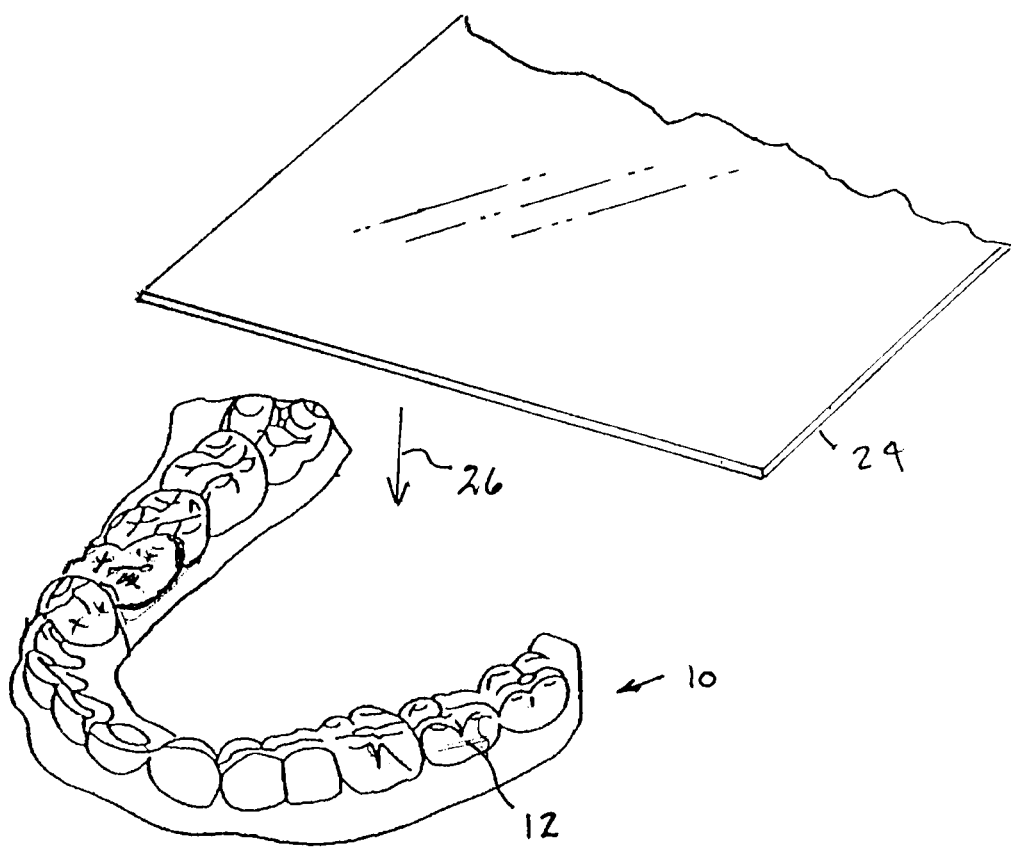
FIG. 4 is a perspective view showing a stage of the fabrication process.

FIG. 1 shows a dental arch model 10 which has been fabricated by a 3-D printing process using commercially available equipment and software.

The 3-D printing process creates dental arch model 10 by a layering process in which a successive layer is laid down on top of a preceding one. Each layer has a finite thickness which can be very small as suggested by a group 12 of layers shown in FIG. 1.

Several of the layers of group 12 are partially shown in FIGS. 1A, 2 and 3 and three of them are identified as a lower layer 14, an intermediate layer 16, and an upper layer 18. Upper layer 18 overlies the immediately underlying intermediate layer 16, and intermediate layer 16 overlies the immediately underlying lower layer 14.

Because the teeth of a person's dental arch represented by arch model 10 have multi-directional curvature, so does the arch model itself. However, because of the nature of 3-D printing, at least a portion of the perimeters of successive layers may not be perfectly blended in a way which creates a perfectly smooth exterior surface. Rather, at least a portion of the perimeter of each such layer is geometrically discontinuous with an immediately underlying portion of the perimeter of the previous layer. This is seen in FIGS. 1A, 2 and 3 on an exaggerated scale where a step-like discontinuity 20 is present between upper layer 18 and intermediate layer 16 and a step-like discontinuity 22 is present between intermediate layer 16 and lower layer 14. These discontinuities create surface grooves in a dental arch model fabricated by a 3-D printing process. While some surface grooves may be quite small so as to present what appears as a smooth surface, they are nonetheless surface discontinuities.

A step in a first embodiment of the fabrication process is shown in FIG. 4 where a sheet 24 of liquid-dissolvable material is about to be applied to arch model 10 as suggested by arrow 26. Sheet 24 is applied to cover at least a portion of the dental arch model by conforming the sheet onto a portion of the dental arch model to physically isolate material from which the dental arch model has been fabricated from material which will be used to fabricate an intra-oral device. The material of sheet 24 also renders the material of the dental arch model and the material for fabricating the intra-oral device immune to chemical reaction with each other. Some examples of suitable materials for sheet 24 are starch, gelatin, and polyvinyl alcohol.

Figure 5:
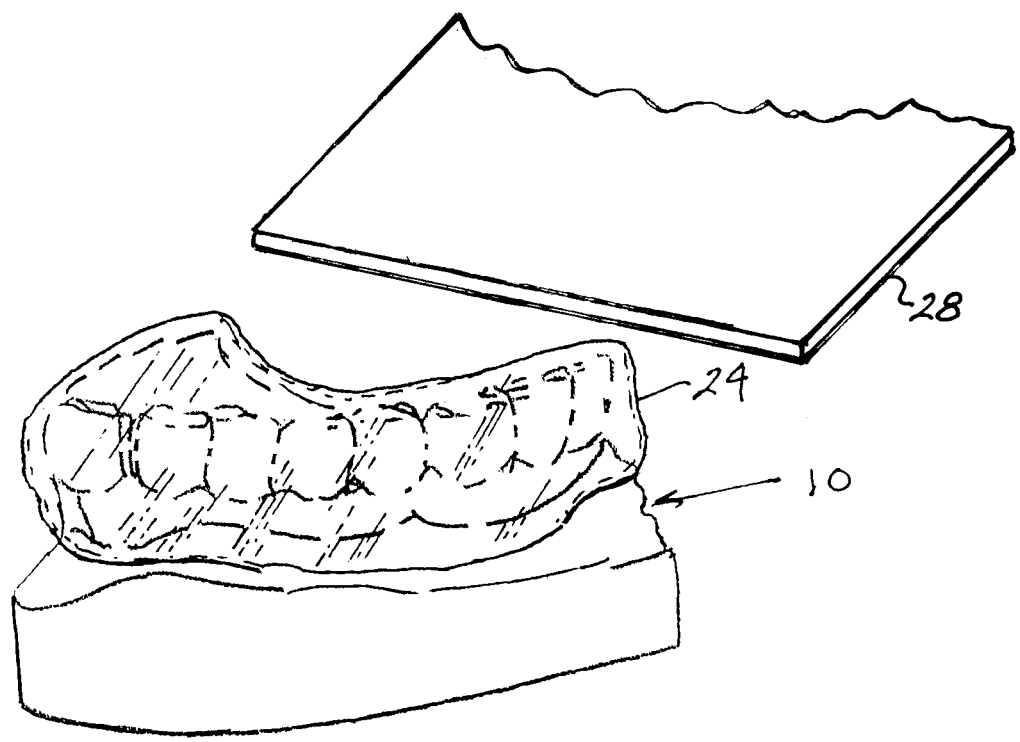
FIG. 5 is a perspective view showing a further stage of the fabrication process.

For illustration only, FIG. 5 shows sheet 24 in a somewhat exaggerated size having been conformed onto dental arch model 10. Sheet 24 is actually sufficiently thin and sufficiently conformed onto the model that the sheet doesn't significantly add to the dimensions of teeth of the arch model. Close conformance of sheet 24 onto arch model 10 may be achieved by using conventional thermal and/or vacuum forming techniques. Material of sheet 24 may be trimmed away as appropriate prior to fabrication of an intra-oral device.

Figure 6:
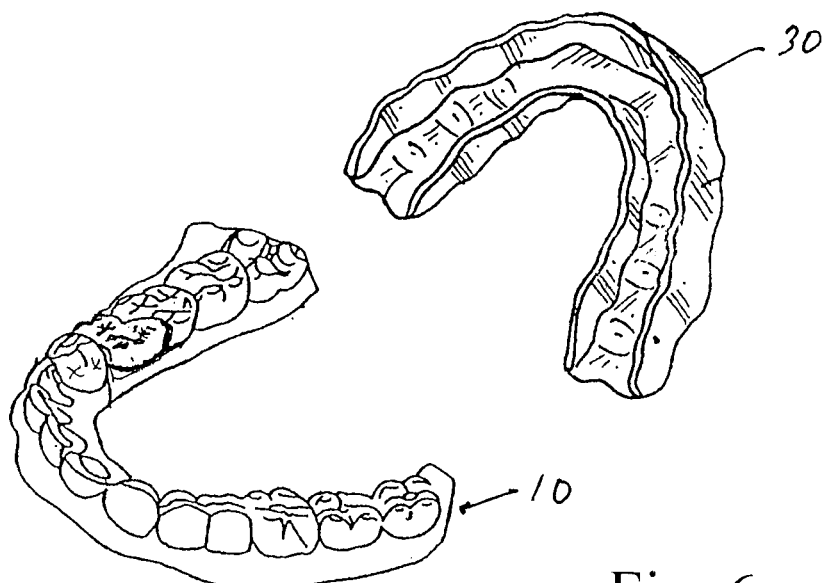
FIG. 6 is a perspective view showing a still further stage of the process.

Once sheet 24 is in place on model 10, an intra-oral device may be fabricated. Material which is used to fabricate the device should not affect the integrity of the sheet material. FIG. 5 shows a sheet of material 28 which is to be formed into a retainer 30 shown in FIG. 6. Sheet 28 is any material suitable for intra-oral use which can be conformed onto sheet 24 to create an arch impression in sheet 28. Once the impression has been taken, the sheet may be treated or cured to cause it to assume a relatively rigid shape which is characteristic of a retainer. It separates from the material of sheet 24 as it is removed from the arch model. The material used to fabricate an intra-oral device may be in other than sheet form.

After removal of a fabricated intra-oral device from the arch model, the liquid-dissolvable material of sheet 24 may remain entirely on the dental arch model, or it may be entirely pulled off with the device, or some may remain on the model while the remainder is pulled off with the device. Any liquid-dissolvable material either on the model or on the device is removed by applying a dissolving liquid to it at temperature for promoting quick dissolution even a temperature exceeding room temperature.

Because starch, gelatin, and polyvinyl alcohol are dissolvable in water, water is used as the dissolving liquid when those materials are used as sheet 24.

Instead of using a sheet 24 of material as a barrier between the dental arch model and the material used to fabricate the intra-oral device as described above, a second embodiment of fabrication process comprises applying a conditioning material to the dental arch model to create the barrier which renders the material of the arch model and the material to be used to fabricate an intra-oral device, immune to chemical reaction with each other. The conditioning material is contained in a solution which is applied to wet the material of the dental arch model and which is then allowed to dry, leaving the conditioning material as a thin coating covering the dental arch model.

The coating will at least partially fill in surface grooves created by the 3-D printing process. The solution is applied is any suitable way such as by spraying it and/or brushing it and/or dabbing it onto the model, and/or dipping the model into it, and then allowing the solution to dry. Once the solution has dried to leave a coating on the model, an additional coating may be applied over the dried one any number of times.

Coating a dental arch model in this way is especially useful for 3D models which have a matte finish, a preferred finish for dental arch models.

The solution has tenacity both to the dental arch model and to any dried underlying coating as the solution dries, and that allows the conditioning material in the solution material to bond to the dental arch model and to any underlying coating. The coating is long-lasting, allowing a coated arch model to be re-used for fabrication of additional and/or other intra-oral devices. However, the coating can be removed by washing it off using soap, detergent, or other comparable cleaning material. The model can later be re-coated.

An example of a suitable solution is a suspension of silica-impregnated wax which may include a drying agent. The wax may be either natural or synthetic.

In order to facilitate removal of a fabricated intra-oral device from a dental arch model which has been coated with a conditioning coating, a release medium is applied as a coating over the underlying conditioning coating. The release medium is one which is compatible with both the conditioning coating and the material to be used to fabricate an intra-oral device.

What is claimed is:

1. A method of fabricating an intra-oral device on a dental arch model, the method comprising:
   fabricating a dental arch model of at least a portion of a person's dental arch by a 3-D printing process which creates multiple consecutive layers of a first material each laid down on top of a preceding layer; forming a barrier on at least a portion of the dental arch model which renders the first material of the dental arch model and a second material to be used to fabricate an intra-oral device immune to chemical reaction with each other; fabricating the intra-oral device by forming the second material onto the portion of the dental arch model onto which the barrier has been formed; and removing the intra-oral device from the dental arch model.

2. A method as set forth in claim 1 in which the step of forming a barrier on at least a portion of the dental arch model comprises conforming a liquid-dissolvable sheet onto a portion of the dental arch model, and then after the intra-oral device has been removed from the dental arch model, applying a dissolving liquid to liquid-dissolvable material remaining on either the dental arch model or the intra-oral device.

3. A method as set forth in claim 2 in which the 3-D printing process creates some consecutive layers with non-congruent perimeters which form surface grooves in the dental arch model, and in which the step of conforming the liquid-dissolvable sheet onto the dental arch model at least partially fills the surface grooves.

4. A method as set forth in claim 3 including using a vacuum to draw the liquid-dissolvable sheet onto the dental arch model.

5. A method as set forth in claim 2 in which the step of applying a dissolving liquid to the liquid-dissolvable sheet comprises applying water as dissolving liquid.

6. A method as set forth in claim 1 in which the step of forming a barrier on at least a portion of the dental arch model comprises wetting the first material of the dental arch model with a solution which will dry to a conditioning coating which renders the first material and the second material used to fabricate an intra-oral immune to chemical reaction with each other.

7. A method as set forth in claim 6 including applying a release coating over the conditioning coating to facilitate removal of the intra-oral device from the dental arch model after fabrication.

8. In a method of fabricating an intra-oral device on a dental arch model, the combination of:
 a 3-D printed dental arch model of at least a portion of a person's dental arch comprising multiple consecutive layers of a first material each laid down on top of a preceding layer; a barrier on at least a portion of the dental arch model which renders the first material of the dental arch model and a second material to be used to fabricate an intra-oral device on the dental arch model, immune to chemical reaction with each other; and an intra-oral device comprising the second material conformed to a portion of the dental arch model covered by the barrier.

9. The combination as set forth in claim 8 in which the barrier comprises a liquid-dissolvable sheet conformed onto a portion of the dental arch model.

10. The combination as set forth in claim 9 in which the liquid-dissolvable sheet is dissolvable in water.

11. The combination as set forth in claim 9 in which the dental arch model comprises some consecutive layers with non-congruent perimeters which form surface grooves in the dental arch model, and in which the liquid-dissolvable sheet at least partially fills the surface grooves.

12. The combination as set forth in claim 8 in which the barrier comprises a dried conditioning coating which renders the first material and the second material immune to chemical reaction with each other.

13. The combination as set forth in claim 12 in which the dental arch model comprises some consecutive layers with non-congruent perimeters which form surface grooves in the dental arch model, and in which the conditioning coating at least partially fills the surface grooves.

14. The combination as set forth in claim 13 including a release coating between the dried conditioning coating and the intra-oral device.

* * * * *